United States Patent
Lange et al.

(10) Patent No.: US 12,173,249 B2
(45) Date of Patent: Dec. 24, 2024

(54) CITRIC ACID-MODIFIED POLYPROPYLENE GLYCOLS

(71) Applicant: LEHMANN&VOSS&CO. KG, Hamburg (DE)

(72) Inventors: Karsten Lange, Wuppertal (DE); Hans Willi Kling, Wuppertal (DE); Susanne Dankert, Stade (DE); Dalibor Vukadinovic-Tenter, Hamburg (DE)

(73) Assignee: LEHMANN & VOSS & CO. KG, Hamburg (DE)

( * ) Notice: Subject to any disclaimer, the term of this patent is extended or adjusted under 35 U.S.C. 154(b) by 0 days.

(21) Appl. No.: 18/552,106

(22) PCT Filed: Mar. 24, 2022

(86) PCT No.: PCT/EP2022/057808
§ 371 (c)(1),
(2) Date: Sep. 22, 2023

(87) PCT Pub. No.: WO2022/200519
PCT Pub. Date: Sep. 29, 2022

(65) Prior Publication Data
US 2024/0174940 A1 May 30, 2024

(30) Foreign Application Priority Data
Mar. 25, 2021 (EP) .................................. 21164845

(51) Int. Cl.
*C10M 145/22* (2006.01)
*A61K 8/85* (2006.01)
(Continued)

(52) U.S. Cl.
CPC ............ *C10M 145/22* (2013.01); *A61K 8/85* (2013.01); *A61Q 5/02* (2013.01); *C07C 69/34* (2013.01); *C10M 101/02* (2013.01); *C10M 169/04* (2013.01); *C10M 2209/102* (2013.01); *C10N 2020/065* (2020.05); *C10N 2030/08* (2013.01); *C10N 2030/12* (2013.01); *C10N 2030/24* (2020.05); *C10N 2040/36* (2013.01)

(58) Field of Classification Search
CPC .............. C10M 145/22; C10M 101/02; C10M 169/04; C10M 2209/102; A61K 8/85; A61Q 5/02; C07C 69/34; C10N 2020/065; C10N 2030/08; C10N 2030/12; C10N 2030/24; C10N 2040/36
See application file for complete search history.

(56) References Cited

U.S. PATENT DOCUMENTS 4,172,802 A 10/1979 Rieder
5,089,531 A 2/1992 Weil
(Continued)

FOREIGN PATENT DOCUMENTS

EP 0199131 A2 10/1986

*Primary Examiner* — Ellen M McAvoy
(74) *Attorney, Agent, or Firm* — Seed IP Law Group LLP

(57) ABSTRACT

The present application relates to citric acid-modified polypropylene glycols which are represented by Formula (1) or, as well as compositions comprising such compounds. The polypropylene glycol-based compounds of the invention are useful as additives and in particular as emulsifying agents in e.g. cooling lubricants, as release agents, as well as additives for cosmetic products.

19 Claims, 4 Drawing Sheets

(51) Int. Cl.
  *A61Q 5/02*   (2006.01)
  *C07C 69/34*   (2006.01)
  *C10M 101/02*   (2006.01)
  *C10M 169/04*   (2006.01)
  *C10N 20/00*   (2006.01)
  *C10N 30/00*   (2006.01)
  *C10N 30/08*   (2006.01)
  *C10N 30/12*   (2006.01)
  *C10N 40/36*   (2006.01)

(56) References Cited

U.S. PATENT DOCUMENTS

| | | | |
|---|---|---|---|
| 5,545,351 A | 8/1996 | Riggs et al. | |
| 6,710,082 B1* | 3/2004 | Pi Subirana | A61K 8/86 424/70.28 |
| 8,192,726 B1* | 6/2012 | O'Lenick | A61K 8/375 424/401 |
| 8,277,787 B1* | 10/2012 | O'Lenick | A61Q 17/04 528/425 |
| 8,367,861 B1* | 2/2013 | O'Lenick | A61K 8/85 424/401 |
| 8,623,342 B1* | 1/2014 | O'Lenick | C08G 63/60 424/70.11 |
| 8,747,822 B1* | 6/2014 | O'Lenick | A61Q 5/12 424/70.11 |
| 2023/0024192 A1* | 1/2023 | Coots | C11D 1/06 |
| 2024/0059998 A1* | 2/2024 | DeBlase | C10M 145/22 |

* cited by examiner

CITRIC ACID-MODIFIED POLYPROPYLENE GLYCOLS

TECHNICAL FIELD

The present invention relates to compounds which are citric acid-modified polypropylene glycols, as well as compositions comprising these compounds. Moreover, the present invention relates to the use of these compounds or compositions as additives and in particular as emulsifying agents for e.g. cooling lubricants, as release agents, or as additives for cosmetic products.

PRIOR ART

Emulsifying agents are compounds or substances which act as a stabilizer for emulsions, thereby preventing immiscible liquids from separating. The addition of emulsifiers finds use in a variety of applications, such as food, health care, as well as fluids such as cooling lubricants for metal working.

Since 2009, the European Union has had the declared goal of significantly increasing the proportion of renewable raw materials in the lubricant and metalworking industries. DIN SPEC 51523, which defines the minimum requirements for biolubricants, was published in 2011.

According to this, a lubricant may only be called a biolubricant if three of the following criteria are met:

Renewable biolubricants must be biobased to a significant extent, i.e. at least 25% must be made from renewable raw materials.

Rapidly biodegradable: biolubricants must be biodegradable to more than 60% according to OECD 301.

Non-hazardous to the environment: Biolubricants must not be classified as hazardous to the environment. This can be demonstrated by testing according to OECD 201/202/203.

Predominantly used oils and emulsifiers (additives) in industry for cooling lubricants are chemically based on mineral oil. Only a few exceptions are known such as MWV DIAZID 1550, a tall-oil based (co-)emulsifier being advertised as sustainable and eco-friendly, but only suitable for a limited number of special applications.

For the above reason, there is a demand for bio-based additives, in particular of emulsifying agents, which are sustainable and environmental-friendly in their preparation, as well as in their use. The additives are preferably multifunctional and can thus be used in different areas. In addition, it should be possible to prepare these additives in an efficient and cost-effective manner from renewable resources. Thus, they make an important contribution to sustainable or more sustainable products in the sense of DIN SPEC 51523.

SUMMARY OF THE INVENTION

The present invention relates to innovative, sustainable additives, in particular emulsifiers for cooling lubricants as well as release agents and additives for cosmetic products, which can be prepared very easily and solves the problems of the prior art by the following means:

In a first aspect, the present invention relates to a propylene glycol-based compound of the following formula:

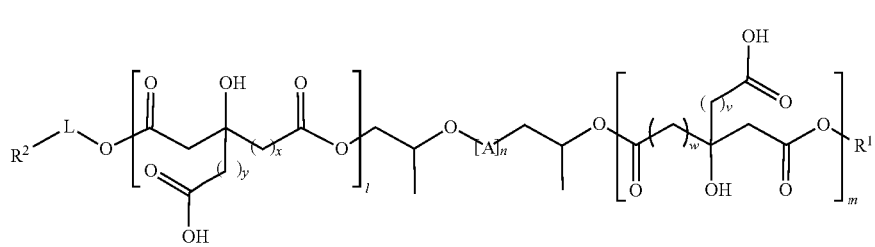

Formula (1)

wherein each A is independently represented by [$CH_2CHCH_3O$] or [$CHCH_3CH_2O$] and wherein n represents the number of propylene oxide repeating units as defined above.

$R^1$ and $R^2$ each independently are hydrogen, a linear or branched $C_{6-34}$ alkyl group which is optionally substituted with OH, a linear or branched $C_{6-34}$ alkenyl group which is optionally substituted with OH, or a group of the formula $N(R^3)$—$C(=O)$—$R^4$;

L is a direct bond, $C(=O)$, $C_{1-10}$ alkylene or a polypropylene oxide unit of the formula $[A]_{n+2}$;

$R^3$ is H, $C_1$-6 alkylene or O—$C_{1-6}$ alkylene;

$R^4$ is a linear or branched $C_{6-34}$alkyl group which is optionally substituted with OH, or a linear or branched $C_{6-34}$alkenyl group which is optionally substituted with OH;

n is an integer from 0-50;

m is 0 or 1, l is 0 or 1, with the proviso that at least one of m and l is 1;

x is 0 or 1, y is 0 or 1 and the sum of x and y is 1 and v is 0 or 1, w is 0 or 1 and the sum of v and w is 1.

Surprisingly, simple condensation reactions of citric acid with liquid and water-miscible polypropylene glycols in different ratios showed that product mixtures were obtained that were well definable, the reactions were well controllable and did not—as expected—react to form much larger polymers (polyesters—as e.g. with PEG'S). By adding further alcohol components such as fatty alcohols or fatty acids, depending on the stoichiometric composition, products of Formula (1) were obtained that were versatile for different applications. The products thus obtained solve the problems of the prior art by providing compounds which are based on renewable resources and are useful as additives in a variety of applications such as emulsifiers in cooling lubricants, as release agents, or as additives for cosmetic products.

In a second aspect, the present invention relates to compositions which comprise at least one of the compounds of Formula (1)

In a third aspect, the present invention relates to the use of the compounds of Formula (1) or compositions comprising these compounds as an additive for a cooling lubricant or release agents.

In a fourth aspect, the present invention relates to the use of the compounds of Formula (1) or compositions comprising these compounds as an additive for cosmetic products.

In a fifth aspect, the present invention relates to the use of the compounds of Formula (1) or compositions containing these compounds as possibly rapidly biodegradable with low toxicity, being condensation products of rapidly biodegradable and harmless reactants.

DETAILED DESCRIPTION OF THE INVENTION

Figure 1:
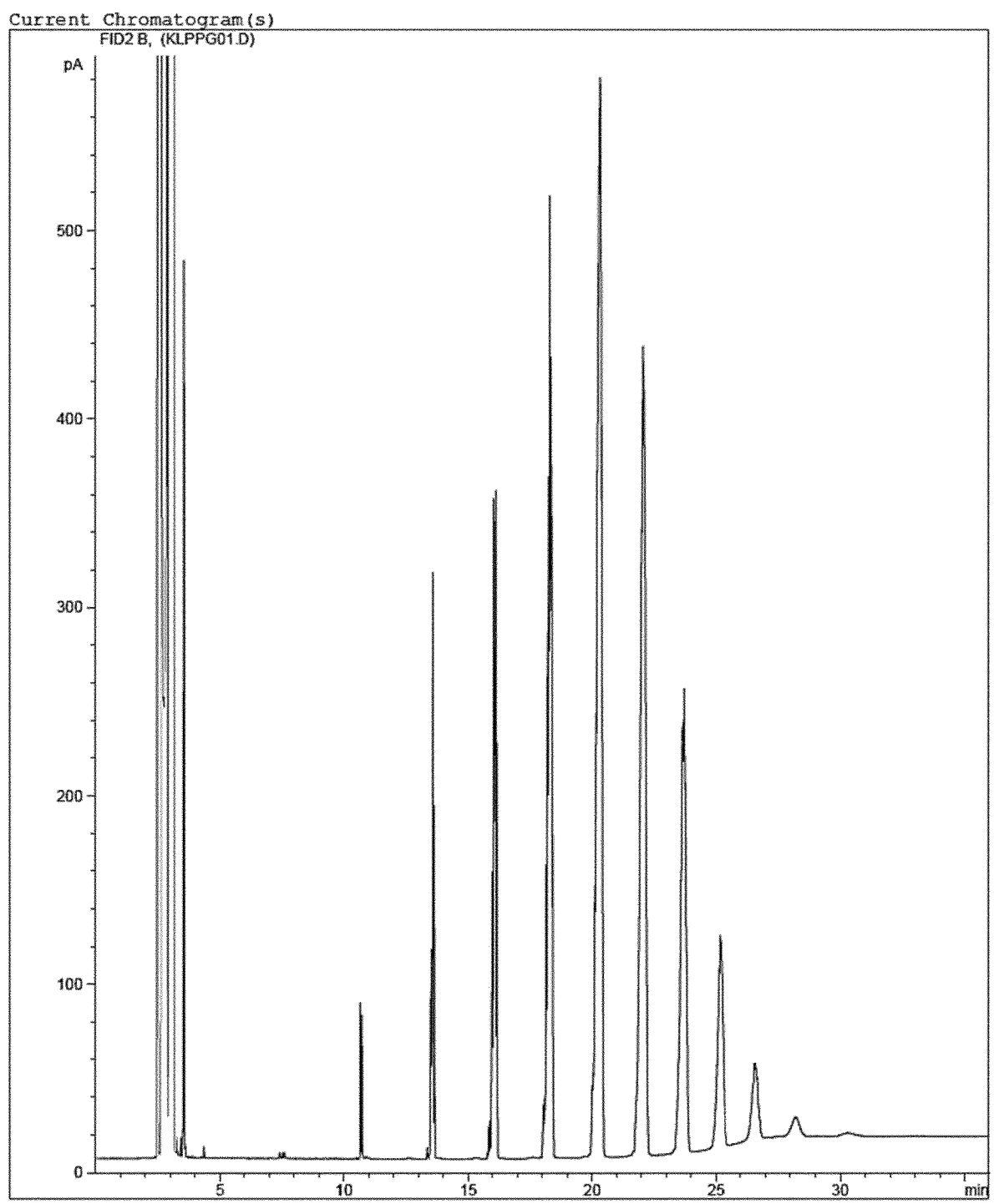
FIG. 1 shows a GC-FID spectrum of PPG 400, measured with a gas chromatograph of the type Agilent G1530A using a Zebron ZB-5_MSI column (30 m×0.25 mm×0.25 μm, max. temperature 370° C., manufactured by Phenomenex®, USA); Flow: 1.6 ml($N_2$)/min; Temp.: 100° C. 1 min, 25 min 100° C.→350° C., 10 min 350° C., Sample Conc.: 5 vol %, Injection 1 μl, splitless

The present invention relates to citric acid-modified polypropylene glycols which are represented by Formula (1)

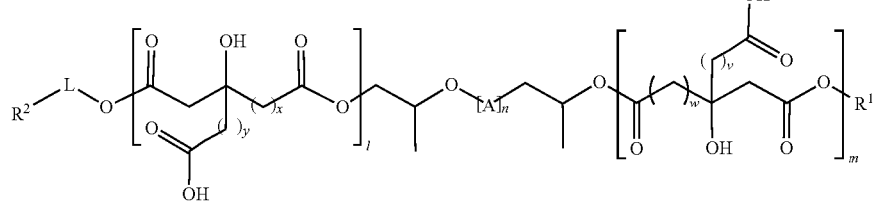

Formula (1)

wherein each A is independently represented by [$CH_2CHCH_3O$] or [$CHCH_3CH_2O$] and wherein n represents the number of propylene oxide repeating units as defined above.

$R^1$ and $R^2$ each independently are hydrogen, a linear or branched $C_{6-34}$ alkyl group which is optionally substituted with OH, a linear or branched $C_{6-34}$ alkenyl group which is optionally substituted with OH, or a group of the formula $N(R^3)$—$C(=O)$—$R^4$;

L is a direct bond, $C(=O)$, $C_{1-10}$ alkylene or a polypropylene oxide unit of the formula [$A$]$_{n+2}$;

$R^3$ is H, $C_{1-6}$ alkylene or O—$C_{1-6}$ alkylene;

$R^4$ is a linear or branched $C_{6-34}$ alkyl group which is optionally substituted with OH, or a linear or branched $C_{6-34}$ alkenyl group which is optionally substituted with OH;

n is an integer from 0-50;

m is 0 or 1, l is 0 or 1, with the proviso that at least one of m and l is 1;

x is 0 or 1, y is 0 or 1 and the sum of x and y is 1 and v is 0 or 1, w is 0 or 1 and the sum of v and w is 1.

In the context of the present invention, the following definitions and test methods apply.

An emulsifier or emulsifying agent (also known as an "emulgent") is a substance that stabilizes an emulsion over time. In an emulsion, one liquid (the dispersed phase) is dispersed in the other (the continuous phase). Emulsifiers can form an emulsion that can exist as "oil-in-water" or "water-in-oil" emulsions, depending on their individual solubility in water and in oil. Emulsifiers that are more soluble in water (and hence, less soluble in oil) will generally form oil-in-water emulsions, while emulsifiers that are more soluble in oil will form water-in-oil emulsions.

In the sense of the present invention, an emulsion is considered stable if no change of size and dispersion of the liquid phase in the continuous phase can be visually detected over a certain time.

Polypropylene glycol (hereinafter abbreviated as "PPG") is a polymer of propylene glycol (also referred to as 1,2-propanediol). PPG has two terminal hydroxyl groups, one of which is attached to a primary carbon, i.e. a primary alcohol function, and the other one is attached to a secondary carbon atom, i.e. a secondary alcohol function. PPG is represented by the following chemical formula:

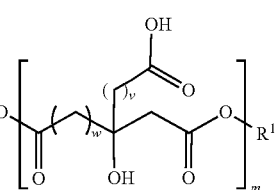

wherein each A is independently represented by [$CH_2CHCH_3O$] or [$CHCH_3CH_2O$] and wherein n represents the number of propylene oxide repeating units as defined above.

PPG may be produced by ring-opening polymerization of propylene oxide or polycondensation of propylene glycol monomers. PPG is commercially available with different average numbers of repeating units n shown in the above formula.

Citric acid (also referred to as 2-hydroxypropane-1,2,3-tricarboxylic acid) is a tricarboxylic acid having the following chemical structure:

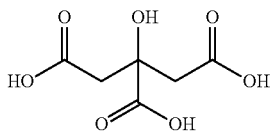

In theory, each of the three carboxylic acid groups can react in an esterification reaction with an alcohol to obtain the respective ester compound. Esterification reactions using citric acid and reaction conditions therefor are well-known to the person skilled in the art.

As described above, a first aspect of the present invention relates to compounds of Formula (1)

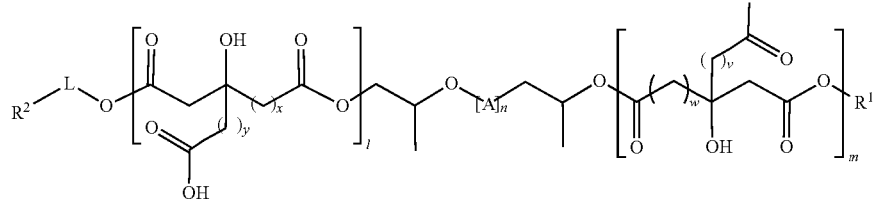

wherein each A is independently represented by [CH$_2$CHCH$_3$O] or [CHCH$_3$CH$_2$O];

R$^1$ and R$^2$ each independently are hydrogen, a linear or branched C$_{6-34}$ alkyl group which is optionally substituted with OH, a linear or branched C$_{6-34}$ alkenyl group which is optionally substituted with OH, or a group of the formula N(R$^3$)—C(=O)—R$^4$;

L is a direct bond, C(=O), C$_{1-10}$ alkylene or a polypropylene oxide unit of the formula [A]$_{n+2}$;

R$^3$ is H, C$_{1-6}$ alkylene or O—C$_{1-6}$ alkylene;

R$^4$ is a linear or branched C$_{6-34}$ alkyl group which is optionally substituted with OH, or a linear or branched C$_{6-34}$ alkenyl group which is optionally substituted with OH;

n is an integer from 0-50;

m is 0 or 1, l is 0 or 1, with the proviso that at least one of m and l is 1;

x is 0 or 1, y is 0 or 1 and the sum of x and y is 1 and v is 0 or 1, w is 0 or 1 and the sum of v and w is 1.

In a preferred embodiment, R$^1$ and R$^2$ each independently are hydrogen, a linear or branched C$_{8-20}$ alkyl group which is optionally substituted with OH, a linear or branched C$_{8-20}$ alkenyl group which is optionally substituted with OH, or a group of the formula N(R$^3$)—C(=O)—R$^4$; L is a direct bond, C(=O), C$_{2-6}$ alkylene or a polypropylene glycol unit of the formula [CH$_2$CH(CH$_3$)O]$_{n+2}$; R$^3$ is hydrogen and R$^4$ is C$_{8-18}$ alkyl or alkenyl.

In Formula (1) and (2), it is preferable that n is 1-20, more preferably 1-10. That is, the compounds of the present invention preferably contain 1-10 polypropylene oxide repeating units which are present in addition to the terminal polypropylene oxide units.

For the compounds of Formula (1), it is preferred that y is 0 and x is 1 and/or v is 0 and w is 1.

The inventors have surprisingly found that the citric acid-modified polypropylene glycol compounds of the present invention exhibit high emulsifying properties and additionally provide high corrosion inhibition. For this reason, the compounds are particularly useful as additives for cooling lubricants. In addition, the compounds of the present invention are multifunctional and can be applied in a variety of further applications, such as cosmetic products. In addition, the compounds of the present invention may be used for the reduction of germ loads in compositions and in particular, cosmetic products. The preparation of the compounds of the present invention is sustainable, efficient and cost-effective.

In the following, compounds of the invention, as well as their preparation and components for their preparation is set out:

Polypropylene Glycol

Commercially available Polypropylene glycol (PPG) is used as a central building block for the compounds of the present invention. The polypropylene glycol used for preparing the present compounds is PPG with n is 1-50, preferably 1-20 and more preferably 1-10 in view of flow characteristics for processability of PPG as a starting material.

In view of the properties of the product of Formula (1) which is produced from PPG, the number-average molecular weight (M$_n$) of PPG may be preferably about 200-800 g/mol, more preferably about 200-400 g/mol, and even more preferably with about 400 g/mol.

The polypropylene glycol which is preferably used for preparing the compounds of the present invention is PPG 400 (also referred to as "P 400") which is technical polypropylene glycol with a Mn of about 400 g/mol. PPG 400 is composed of polymers having mainly three to twelve propylene oxide units. That is, in the above formula of PPG, n is 1-10.

The Gaussian-like distribution of the polymer components with different numbers of propylene oxide units in PPG 400 is shown in the GC (FID) chromatogram in FIG. 1.

In FIG. 1, the peak at 10.7 min represents tripropylene glycol (n=1 in the above formula of PPG) and each subsequent peak is the homologous compound with one additional propylene oxide unit (n+1). The largest signals can thus be assigned to hexapropylene oxide (n=4) and heptapropylene oxide (n=5):

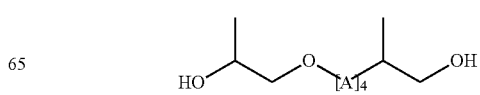

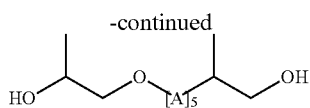

each A is independently represented by [CH$_2$CHCH$_3$O] or [CHCH$_3$CH$_2$O]

Citric Acid-Modified Polypropylene Glycol ("CaPPGb")

In one embodiment of the invention, the compound of Formula (1) is a citric acid-modified PPG. That is, in Formula (1) R$^1$ and R$^2$ are hydrogen, m is 0 or 1 and l is 0 or 1, with the proviso that at least one of m and l is 1.

Citric acid-modified PPG are obtained by reacting PPG and citric acid in a condensation reaction, wherein PPG and citric acid are used in equivalent amounts or either thereof in an excess amount and the mixture is usually stirred for 15 mins to 4 hours, preferably 1.5 to 3 hours, at a temperature of 100-200° C., preferably 150° C., without the addition of a solvent. The stoichiometric composition of the resulting products is defined as "CaPPGb", wherein a indicates the equivalents of citric acid and b indicates the equivalents of PPG used in the reaction for preparing citric acid-modified PPG.

Preferably, compounds of the composition C$_a$PPG$_b$ are obtained by reacting 1 to 2 molar equivalents citric acid with 1 to 2 molar equivalents. More preferably, the citric acid-modified polypropylene glycol compound of the present invention conforms to a stoichiometric composition of C1PPG1, C2PPG1 or C1PPG2.

That is, C1PPG1 indicates that the compound is obtained by condensation reaction of 1 equivalent citric acid and 1 equivalent PPG. For C1PPG1, in Formula (1), R$^1$ is hydrogen, R$^2$ is hydrogen, L is a direct bond, m is 0 and l is 1 or m is 1 and l is 0.

C2PPG1 is obtained by condensation reaction of 2 equivalents citric acid and 1 equivalent PPG. For C2PPG1, in Formula (1), R$^1$ is hydrogen, R$^2$ is hydrogen, L is a direct bond, m is 1 and l is 1.

C1PPG2 is obtained by condensation reaction of 1 equivalent citric acid and 2 equivalents PPG. For C1PPG2, in Formula (1), R1 is hydrogen, R2 is hydrogen, L is a polypropylene oxide unit of the formula [A]$_{n+2}$, m is 0 and l is 1.

Most probable structures of these compounds are shown below:

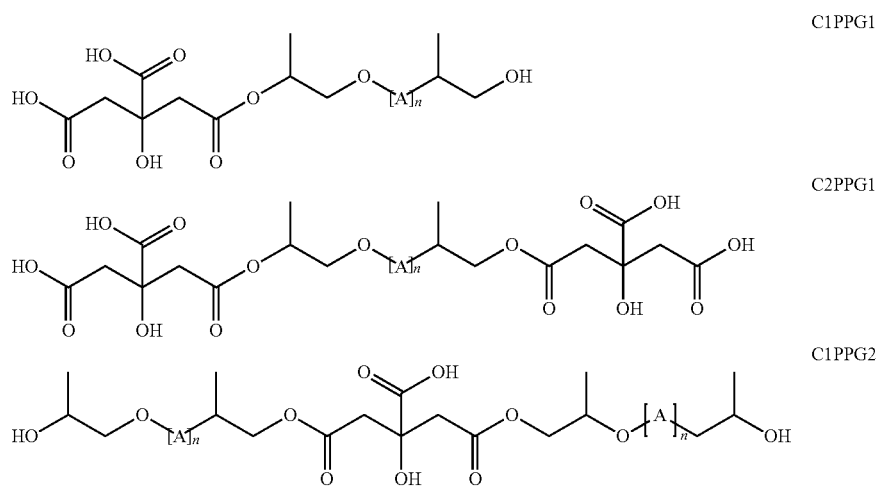

wherein each A is independently represented by [CH$_2$CHCH$_3$O] or [CHCH$_3$CH$_2$O] and wherein n represents the number of propylene oxide repeating units as defined above.

The inventors have surprisingly found that the citric acid-modified PPG compounds of the present invention are provided with highly desirable properties. Specifically, C1PPG1, C2PPG1 and C1PPG2 were found to be suitable as additives and in particular as (co-) emulsifying agents and solubilizers for oil-based compositions, such as cooling lubricants. From the above compounds, P1PPG1 is particularly preferred from the viewpoint of emulsifying properties.

In addition, it was surprisingly found that the compounds of the present invention having a structure of "C$_a$PPG$_b$" provided a germ load reducing efficacy when used as an additive in a composition. From the viewpoint of germ load reducing efficacy, it is preferred that 2.5 wt % of the citric acid-ester are used as an additive, based on the total weight of the composition. In addition, with regard to the germ load reducing efficacy, it is preferred that C$_2$PPG$_1$ is used as an additive.

Fatty Acid Modified Citric Acid Ester of Polypropylene Glycols

In another embodiment of the invention, the compound of Formula (1) is a citric acid ester of PPG which is modified with a fatty acid, a fatty alcohol or a fatty alkanolamide.

In one preferred embodiment, the compound of Formula (1) is a citric acid ester of PPG which is modified with a fatty acid (hereinafter abbreviated as "FSPPGC"). That is, in Formula (1) $R^1$ is hydrogen, $R^2$ is a linear or branched C6-34alkyl group which is optionally substituted with OH, a linear or branched C6-34alkenyl group which is optionally substituted with OH, a linear or branched C8-20 alkenyl group, L is C(=O), m is 1 and l is 0.

In the present invention, "which is optionally substituted with OH" means that the specified group is unsubstituted or has one or more hydroxyl substituents. This equally applies to the following.

Preferably, $R^2$ is a linear C8-20 alkyl group which is optionally substituted with OH, a linear C8-20 alkenyl group which is optionally substituted with OH. More preferably, $R^2$ is a linear C11-17 alkyl group.

In another preferred embodiment, $R^2$ is a linear C11-17 alkenyl group which is optionally substituted with OH. More preferably, $R^2$ is a monosaturated C18 alkenyl group which is optionally substituted with OH. That is, $R^2$ represents an alkyl group which includes one double bond in its chain. The double bond(s) present in the alkenyl group may individually have either (E)- or (Z)-configuration. This equally applies hereinafter.

FSPPGC compounds of the invention are prepared by first reacting PPG in equivalent amounts with a fatty acid, followed by reacting the resulting product with citric acid.

The reaction is carried out by stirring a mixture of PPG and the fatty acid for 0.5 to 4 hours, preferably 2 hours, at a temperature of 100-200° C., preferably 150° C., in the presence of p-toluenesulfonic acid (pTSA) as a catalyst without the addition of a solvent in an open receptacle. Then, citric acid is added in an equivalent amount and the reaction mixture is stirred for 0.5-3 hours, preferably 1 hour at the same temperature.

Reaction equation and one possible structure of FSPPGC product mixture in accordance with the present invention and its preparation from PPG, a fatty acid $R_2COOH$ and citric acid is shown below:

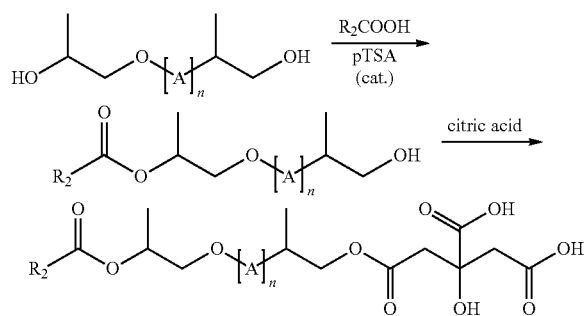

wherein each A is independently represented by [CH$_2$CHCH$_3$O] or [CHCH$_3$CH$_2$O] and wherein n represents the number of propylene oxide repeating units as defined above. $R^2$ represents an alkyl or alkenyl group as defined above.

Fatty acids (in the above scheme represented as R$_2$COOH) which are useful in preparing the compounds of the present invention include, but are not limited to, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, ricinoleic acid or the like.

Among those, lauric acid, palmitic acid, stearic acid, oleic acid and ricinoleic acid are preferred. That is, in a preferred embodiment, the compound of Formula (1) is a FSPPGC compound with R2 being represented by C12H25 (12:0), C15H31 (16:0), C17H35 (18:0), C17H33 (18:1) or C17H33O (18:1, 12-OH), respectively. The numbers in brackets show the number of carbon atoms to the number of double bonds of the fatty acid $R_2$—COOH used in the preparation reaction of the FSPPGC compound.

The inventors have surprisingly found that the FSPPGC compounds of the present invention exhibit highly desirable properties. Specifically, these compounds provide stable (co)emulsifying properties and in addition, have excellent anti-corrosive properties.

From the viewpoint of anti-corrosive properties, lauric acid and palmitic acid are even more preferred to be used as the fatty acid for the above compounds. Hence, in the above formula, $R^2$ preferably represents a linear alkyl group having the formula $C_{11}H_{23}$ or $C_{15}H_{31}$.

Fatty-Alcohol Modified Citric Acid Ester of Polypropylene Glycols

In another preferred embodiment, the compound of Formula (1) is a citric acid ester of PPG which is modified with a fatty alcohol (hereinafter abbreviated as "PPGCFA"). That is, in Formula (1) $R^1$ is hydrogen, $R^2$ is a linear or branched C6-34alkyl group which is optionally substituted with OH, a linear or branched C6-34alkenyl group which is optionally substituted with OH, L is a direct bond, m is 0 and l is 1.

Preferably, $R^2$ is a linear or branched $C_{8-18}$ alkyl group which is optionally substituted with OH, a linear or branched $C_{8-18}$ alkenyl group which is optionally substituted with OH.

PPGCFA compounds of the invention are prepared by first reacting PPG in equivalent amounts with citric acid to obtain $C_1PPG_1$ as described above. To $C_1PPG_1$, an equivalent amount of fatty alcohol is subsequently added, and the reaction mixture is stirred for another 2 to 3 hours, preferably 2.5 hours, at the same temperature.

Reaction equation and one possible structure of PPGCFA product mixture in accordance with the present invention and its preparation from PPG, a fatty alcohol $R_2$—OH and citric acid is shown below:

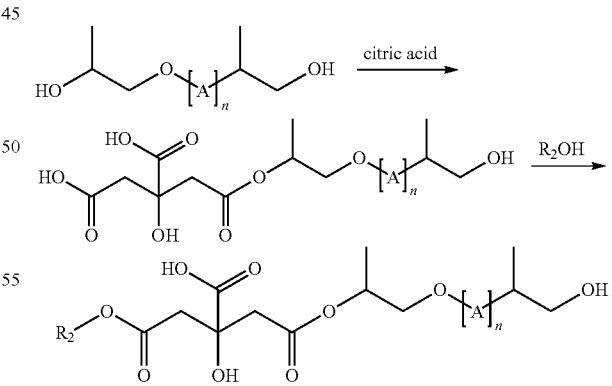

wherein each A is independently represented by [CH$_2$CHCH$_3$O] or [CHCH$_3$CH$_2$O] and wherein n represents the number of propylene oxide repeating units as defined above. $R_2$ represents an alkyl or alkenyl group as defined above.

Fatty alcohols (in the above scheme represented as $R_2$—OH) which are useful in preparing the compounds of the present invention include, but are not limited to, octanol, decanol, dodecanol, tetradecanol, hexadecanol, octadecanol, oleyl alcohol and linoleyl alcohol. That is, in the above formula of PPGCFA, $R_2$ represents an alkyl group having the formula $C_{10}H_{21}$, $C_{12}H_{25}$, $C_{14}H_{29}$, $C_{16}H_{33}$ or $C_{18}H_{37}$, respectively, or an alkenyl group having the formula $C_{18}H_{35}$ or $C_{18}H_{33}$, respectively.

The inventors have found that the above PPGCFA compounds provide desirable (co-) emulsifying properties. In view of emulsifying properties, decanol and dodecanol are preferably used as the fatty alcohol among the above compounds. Thus, in the PPGCFA compounds of the present invention $R^2$ is preferably a linear alkyl group of the formula $C_{10}H_{21}$ or $C_{12}H_{25}$.

Fatty Acid Alkanolamide Modified Citric Acid Ester of Polypropylene Glycols

In a further preferred embodiment of the invention, the compound of Formula (1) is a citric acid ester of PPG which is modified with a fatty alkanolamide (hereinafter abbreviated as "PPGCFSA"). That is, in Formula (1) $R^1$ is hydrogen, L is $C_{1-10}$ alkylene, $R^2$ is $N(R^3)$—$C(=O)$—$R^4$, wherein $R^3$ is H, $C_{1-6}$ alkylene or O—$C_{1-6}$ alkylene, $R^4$ is a linear or branched $C_{6-34}$ alkyl group which is optionally substituted with OH, or a linear or branched $C_{6-34}$ alkenyl group which is optionally substituted with OH, and l is 1 and m is 0.

Preferably, for the PPGCFSA compounds $R^1$ in Formula (1) is hydrogen, $R^2$ is a linear or branched $C_{8-20}$ alkyl group which is optionally substituted with OH, a linear or branched $C_{8-20}$ alkenyl group which is optionally substituted with OH, L is $C_{2-6}$ alkylene and $R^2$ is $N(R^3)$—$C(=O)$—$R^4$, wherein $R^3$ is hydrogen and $R^4$ is a $C_{8-18}$ alkyl or alkenyl group, l is 1 and m is 0. Even more preferably, for the PPGCFSA compounds L is $C_{2-3}$ alkylene and most preferred $C_2$ alkylene.

PPGCFSA compounds of the invention are prepared in a similar manner to PPGCFA compounds. Specifically, the compounds are prepared by reacting PPG in equivalent amounts with citric acid to obtain $C_1PPG_1$ as described above. To $C_1PPG_1$, an equivalent amount of fatty acid alkanolamide (hereinafter abbreviated as "FSA") is added and the reaction mixture is stirred for another 2 to 6 hours, preferably 5 hours, at the same temperature as indicated above and preferably at a temperature of 150° C.

The FSA can be obtained by reacting a fatty acid methyl ester (R(C=O)OMe) with an amino alcohol at a temperature of about 160° C. for 5 to 6 hours. An exemplary preparation for the FSA from fatty acid methyl esters ($R^4$(C=O)OMe) using an ethanolamine derivative is shown below.

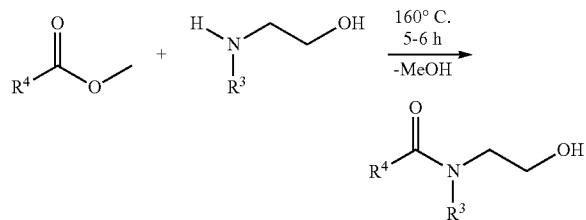

wherein $R^3$ and $R^4$ are defined as above for Formula (1).

Fatty acid methyl esters which may be used for preparing FSA include methyl esters derived from plant-based oils such as rapeseed oil, sunflower oil, sunflower oil with high oleic acid content and ricinus oil (also known as castor oil) but are not limited thereto. These plant-based oils usually contain various fatty acids, such as palmitic acid, stearic acid, oleic acid, linoleic acid, linolenic acid and the like. Thus, for the PPGCFSA compounds $R^4$ is preferably an alkyl or alkylene group which is derived from these plant-based oils.

Various amino alcohols which include an $C_{1-10}$ alkylene group can be used for preparing the FSA. For the compounds of the present invention, the amino alcohol used is preferably ethanolamide or propanolamide and more preferably ethanolamide. Hereinafter, the FSA are labelled according to the fatty acid or plant-based oil from which the methyl ester is derived and the amino alcohol used for preparation. For example, "oleic acid propanolamide" means that the FSA is obtained from oleic acid methyl ester and propanolamide.

One possible structure of PPGCFSA compounds in accordance with the present invention is shown below:

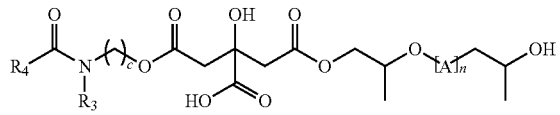

wherein each A is independently represented by [$CH_2CHCH_3O$] or [$CHCH_3CH_2O$], wherein n represents the number of propylene oxide repeating units as defined above and wherein $R^3$ and $R^4$ are defined as above and c represents the number of carbon atoms in the alkylene unit defined for L. That is, for L being $C_{1-10}$ alkylene c is an integer of 1-10.

The inventors have found that the PPGCFSA compounds of the present invention surprisingly exhibit highly desirable emulsifying and anti-corrosive properties.

In a second aspect, the present invention relates to compositions which comprise at least one of the compounds of Formula (1). For example, the composition may be a mixture of compounds of Formula (1) which is obtained by condensation reaction of 1 to 2 equivalents polypropylene glycol and 1 to 2 equivalents citric acid and optional condensation reaction of the product resulting therefrom with a fatty acid, a fatty alcohol or a fatty alkanolamide.

Depending on the desired use, the compositions of the present invention may contain further components in addition to the compounds of the present invention. For example, the composition may be used as cooling lubricant. For such use, the compositions preferably contain a base oil and at least one of the compounds of Formula (1) described above. Examples for the base oil are mineral oil, rapeseed oil or rape methyl ester (RME), but are not limited thereto.

The compounds of Formula (1) are preferably contained in the composition in an amount of 1-50 wt %, preferably 5-25 wt % and even more preferably about 20 wt %, based on the weight of base oil in the composition.

In a preferred embodiment, the composition further contains a base for pH adjustment of the composition. Examples for bases which can be added to the composition include potassium hydroxide or triethylamine but are not limited thereto. Preferably, the base added to the composition is triethylamine.

The composition may optionally contain one or more additives, selected from emulsifiers, solubilizing agents, anti-corrosive agents and preservatives.

Examples of the emulsifier which can be comprised in the compositions of the present invention are tall oil and oleic acid but are not limited thereto. Solubilizing agents which may be added to the compositions are RME, oleic alcohol, mixtures of branched C16-20 alcohols, octanoic acid, isononanoic acid and PPG 400, but are not limited thereto. Examples of anti-corrosive agents include octanoic acid, isononanoic acid, 3-amino-4-octanol and ethanolamine.

In a third aspect, the present invention relates to the use of the compounds of Formula (1) or compositions comprising these compounds as an additive for a cooling lubricant or a release agent. As will be shown in the exemplary section of the present application, the inventors have found that the compounds of Formula (1) are particularly useful as additives for cooling lubricants, in particular in the form of cooling lubricant concentrates, due to their emulsifying properties. Cooling lubricants which are also known as cutting fluids are types of coolants and lubricants which are used in metalworking process. As the compounds and compositions of the present invention provide anti-corrosive properties and thus, prevent rusting in metal, they are considered particularly useful for this application.

In a fourth aspect, the present invention relates to the use of the compounds of Formula (1) or compositions comprising these compounds as an additive for cosmetic products. For example, the compound or composition of the present invention may be added in an amount of 0.5-5 wt % to a raw material, based on the amount of raw material. Preferably, the amount of compound is 2-2.5 wt %, based on the weight of raw material. For example, a raw material for which the compounds of Formula (1) or compositions comprising the compounds may be useful is fibre material which can be used for cosmetic products. Specifically, the additive may provide a beneficial germ load reducing effect when used as an additive for raw material which has a high germ load due to its production method.

In addition, the compounds or composition may be used as an additive for hair care products, such as shampoo. Due to the germ load reducing effect of the compounds or compositions of the invention, their use in cosmetic products is beneficial as it prevents an increase in germ load of the product. In particular, the compound or composition of the present invention may be added in an amount of 1-5 wt % to a cosmetic product, based on the weight of cosmetic product. In view of a beneficial germ load reducing effect, the amount is preferably 2-2.5 wt %, based on the weight of the cosmetic product.

In summary, one important aspect of the present invention resides in the discovery that the compounds of Formula (1) and in particular $C_aPPG_b$, FSPPGC, PPGCFA and PPGCFSA as described above exhibit excellent emulsifying properties and hence can be used as additives for a cooling lubricant. In addition, the compounds provide anti-corrosive properties and hence are specifically suitable to be present as an additive in cooling lubricants.

In addition, it was surprisingly found that compounds that were microbiologically tested in provide a germ load reducing effect in that they prevent an increase in germ load or even reduce the germ load in compositions.

EXAMPLES

Example Section 1—Preparation of Example Compounds of Formula (1)

Exemplary preparations of example compounds of Formula (1) and their analysis are set out in detail below. The compounds which are not included below but listed above as exemplary compounds, were prepared in accordance with the below methods using the respective starting materials explained above.

1. Preparation of C1PPG1

In a 2000 ml open beaker, 384 g (2 mol) citric acid were added to 800 g PPG 400 (2 mol) and the mixture was stirred for 150 mins at 150° C. After cooling down, the thus obtained product mixture was used without further purification steps.

2. Preparation of PPG C HC

In a 250 ml open beaker, 23.6 g (0.12 mol) citric acid were added to 49.2 g (0.12 mol) PPG 400 and the mixture was stirred for 20 mins at 150° C. Then, 31.5 g (0.12 mol) hexadecanol were added and the mixture was stirred for 3 h and 40 mins at 150° C. After cooling down, the thus obtained product mixture was used without further purification steps.

3. Preparation of PPG C OA

In a 250 ml open beaker, 23.0 g (0.12 mol) citric acid were added to 48.0 g (0.12 mol) PPG 400 and the mixture was stirred for 20 mins at 150° C. Then, 33.6 g (0.12 mmol) oleyl alcohol were added and the mixture was stirred for 3 h and 40 mins at 150° C. After cooling down, the resulting product mixture was used without further purification steps.

4. Preparation of Rapeseed-Ethanolamide REA

In a 500 ml single-neck flask with distillation bridge 200 g of Rapeseed methylester (0.65 mol) and 37 g (0.62 mol) Ethanolamine are heated up to 160° C. and stirred for 5 h under continuous distillation of methanol. After cooling down, the resulting product mixture was used without further purification steps.

5. Preparation of PPGCREA

In a 250 ml open beaker, 23.0 g (0.12 mol) citric acid were added to 48.0 g (0.12 mol) PPG 400 and the mixture was stirred for 20 mins at 150° C. Then, 39 g (0.12 mmol) REA were added and the mixture was stirred for further 3.5 h at 150° C. After cooling down, the resulting product mixture was used without further purification steps.

The quality of the reaction mixtures was analysed by determining the acid number and comparing the acid number with the theoretically calculated acid number.

6. General Procedure for Determining the Acid Number (AN):

The term "acid number" (AN) is used to quantify the acidity of a substance and is determined by the molar amount of base that is needed to neutralize the acids in one gram of a substance. In the present invention, the AN is used to determine the amount of free carboxylic acid groups and thus the degree of esterification of a prepared condensation product. The AN was determined by dissolving a precisely weighed quantity between 0.500 to 0.900 g of substance in an ethanol/water mixture (20/80) and titration against aqueous sodium hydroxide solution having a concentration of 0.1 mol/l in the presence of phenolphthalein as an indicator. The amount of NaOH necessary to neutralize the dissolved substance is used to calculate the molar amount of free carboxylic acid groups in the substance as follows: AN=[c(NaOH)×V(NaOH)]/m(substance)

wherein c(NaOH) represents the concentration of the sodium hydroxide solution, V(NaOH) the volume of the sodium hydroxide solution necessary to neutralize the substance during titration and m represents the mass of substance dissolved for determining the AN.

The theoretical acid number was obtained by calculating the theoretically necessary amount of NaOH necessary for neutralizing the carboxylic acid groups present in the most likely structure. Calculations: theor. AN=$(1/M_n)$×(number of free acid groups)

The acid number and the theoretical acid number of some exemplary prepared compounds of the present invention are shown in Table 1 below:

TABLE 1

| compound ($M_n$ [g/mol]) | AN [mmol acid/g] | theoretical AN [mmol acid/g] |
|---|---|---|
| C1PPG1 (574) | 3.68 | 3.48 |
| C2PPG1 (748) | 5.38 | 5.35 |
| LS PPG C (756) | 2.97 | 2.64 |
| PS PPG C (812) | 2.39 | 2.46 |
| SS PPG C (840) | 2.20 | 2.38 |
| OS PPG C (838) | 2.51 | 2.38 |
| RS PPG C (854) | 2.22 | 2.34 |
| PPG C DC (714) | 1.88 | 1.45 |
| PPG C DD (742) | 1.79 | 1.35 |
| PPG C HD (798) | 1.46 | 1.25 |
| PPG C OD (826) | 1.40 | 1.21 |
| PPG C OA (824) | 1.85 | 1.21 |

Comparison of the determined acid numbers and the theoretically calculated acid number indicates that the molar amount of free carboxylic acid corresponded to the proposed structures and thus the desired compounds were obtained.

Example Section 2—Evaluation of the Properties of the Compounds of the Present Invention In order to evaluate the properties of the invention, so-called concentrates were first prepared in accordance with the usual methods of the lubricant industry, i.e. homogeneous and transparent mixtures of substances consisting mainly of a dominant oil phase, all the necessary additives and even small quantities of water. Usually, these are microemulsions. These concentrates are then diluted with water to produce emulsions with an oil content of 5-10%, which are used in this way in technical processes (such as metal processing).

General Procedure for Testing the Stabilizing and the Emulsifying Properties of the Compounds of the Present Invention Example Concentrates—Based on Mineral Oil

| C1: | 30 g Nynas T22 | C2: | 30 g Nynas T22 |
|---|---|---|---|
| | 12 g Talloil | | 9 g Talloil |
| | 2 g oleyl alcohol | | 2 g oleyl alcohol |
| | 1 g PPG400 | | 1 g PPG400 |
| | 6 g Triethanolamine | | 6 g Triethanolamine |
| | 10 g Water | | 3 g Water |
| | 6 g PPGCDC | | 6 g PPGCDD |

Figure 4:
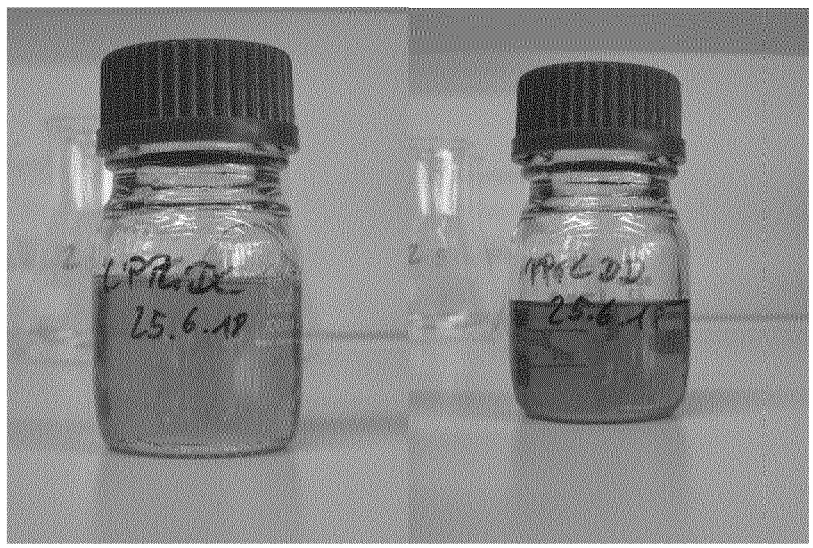
FIG. 4 shows pictures of concentrates C1 and C2 after 3-month storage at 40° C.

For the preparation of the concentrates, the components listed above were added in this order at room temperature (RT) under continuous stirring. To evaluate the stability, the prepared mixtures were stored at 40° C. in a drying cabinet. Stability of concentrates (SOC) has been obtained over time. See FIG. 4

The concentrates were subsequently diluted to 5% emulsions with water, stored at RT in a sealed measuring cylinder and the stability of the emulsions was assessed by observation over a period of time. Resulting pH values and stability of emulsions (SOE) and have been determined.

Figure 5:
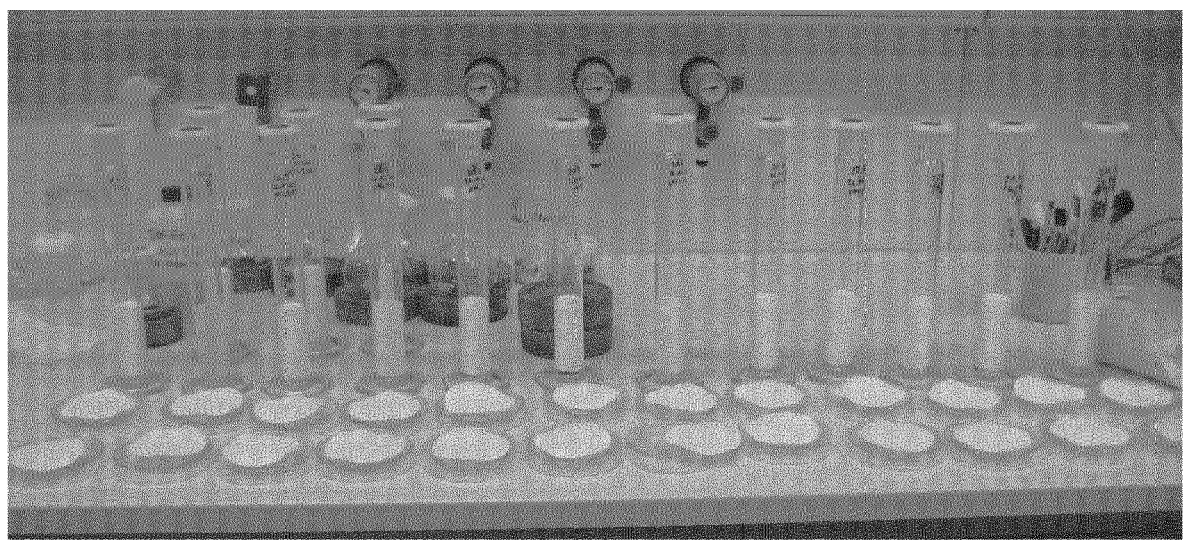
FIG. 5 shows typical emulsion tests with subsequent corrosion test (in the foreground the filter papers used for this purpose)

Part of the emulsions were then used for tests according to DIN 51360-2 to determine their corrosion properties. See FIG. 5. Degree of corrosion (DOC) was identified. The results were listed in following table:

| | SOC | pH value | SOE | DOC |
|---|---|---|---|---|
| C1: | >6 month | 7.9 | >42 days | 0 (no corrosion) |
| C2: | >6 month | 8.1 | >42 days | 0 (no corrosion) |

Example Concentrates—Based on Rapeseed Oil

| C3: | C4: |
|---|---|
| 30 g Rapeseed oil | 30 g Rapeseed oil |
| 5 g olic acid | 2 g olic acid |
| 14 g Triethanolamine | 10 g Triethanolamine |
| 4 g Water | 2 g Water |
| 8 g PPG 400 | 4 g PPG 400 |
| 5 g PPGC | 6 g PPGCOA |
| 6 g PPGCDC | |

The next concentrates C3 and C4 were prepared in analogy to C1 and C2 at RT. Stability of concentrates (SOC) at 40° C. has been obtained over time. pH values and stability of resulting emulsions (SOE) and have been determined. The results were listed in following table:

| | SOC | pH value | SOE |
|---|---|---|---|
| C3: | >30 days | 8.5 | >30 days |
| C4: | >30 days | 8.0 | >30 days |

Example Concentrates—Based on Rapeseed-Methylesters (RME)

| C5: | C6: |
|---|---|
| 30 g Rapeseed-methylesters | 30 g Rapeseed-methylesters |
| 14 g olic acid | 1 g olic acid |
| 13 g Triethanolamine | 3 g Triethanolamine |
| 3.5 g Water | 1 g Water |
| 2 g PPGC | 3 g PPGCRPA |
| 6 g PPGCDC | |

Next concentrates C5 and C6 were prepared in analogy to C1 and C2 at RT. Stability of concentrates (SOC) at 40° C. has been obtained over time. pH values and stability of resulting emulsions (SOE) and have been determined. The results were listed in following table:

| | SOC | pH value | SOE |
|---|---|---|---|
| C5: | >30 days | 8.5 | >30 days |
| C6: | >7 days | 8.9 | >7 days |

Emulsions with a higher RME-phase content of 30% were also prepared from concentrate C5. These also showed stabilities >30 days.

Example Section 3—Anti-Corrosive Properties

In addition, the anti-corrosive ability of some compounds was tested. For this purpose, a test system (oil-phase and emulsion) has been developed. The therefore used oil phase had following composition:

| Oil-phase | m [g] | wt [%] |
|---|---|---|
| Nynas T22 | 30.0 | 77.0 |
| Tween 65 | 6.0 | 15.0 |
| test compound | 3.0 | 8.0 |
| sum | 39.0 | 100.0 |

5 g of each test oil phase was diluted and homogenised with 94 g of water and 1 g of triethanolamine. The emulsions were then tested according to DIN 51360-2 and rated on a customized scale of 1-4, with 0 indicating no anti-corrosive properties and 4 indicating maximum anti-corrosive properties (non-corrosive). In order to unequivocally assign the anti-corrosive properties to the compounds of the present invention, components and additives were equally tested. The results of the used components and additives are listed in following table:

| components | 0 | 1 | 2 | 3 | 4 |
|---|---|---|---|---|---|
| Nynass T22 | x | | | | |
| RME | x | | | | |
| rapeseed oil | x | | | | |
| PPG | x | | | | |
| oleyl alcohol | x | | | | |
| olein | x | | | | |
| TEA | | | x | | |
| EA | | | | | x |
| tall oil | | x | | | |
| Isofol 18T | x | | | | |
| Isononanic acid | | | | x | |
| Corrguard | | | | | x |
| Tergitol | | x | | | |
| Prifac (octanoic acid) | | | | | x |
| Tween 65 | x | | | | |

Table of anti-corrosive properties to the compounds of present invention:

| | 0 | 1 | 2 | 3 | 4 |
|---|---|---|---|---|---|
| PPG C DC | | | x | | |
| PPG C DD | | x | | | |
| PPG C HD | | x | | | |
| PPG C OD | | x | | | |
| PPG C OA | | x | | | |
| PPG C OPA | | x | | | |
| PPG C OEA | | x | | | |
| PPG C RPA | | x | | | |
| PPG C REA | | | | | x |
| PPG C SPA | | | | | x |
| PPG C SEA | | | | | x |
| PPG C RiEA | | x | | | |
| LS PPG C | | | | | x |
| PS PPG C | | | | | x |
| SS PPG C | | x | | | |
| OS PPG C | | x | | | |
| RS PPG C | | | | x | |
| C1 PPG1 | | | | x | |
| C2 PPG1 | | x | | | |

From the above results, it can be taken that lots of the compounds of the present invention show anti-corrosive properties under those mentioned conditions. Specifically, compounds of the structure PPGCFSA and in particular PPGCREA, PPGCSPA and PPGCSEA, have shown excellent anti-corrosive properties. In addition, compounds of the structure FSPPGC based on lauric acid and palmitic acid (LS PPG C and PS PPG C) have shown excellent anti-corrosive properties, too. Further studies have shown that the effect of the substances correlates with their concentration.

Example Section 4—Germ Load Evaluation

For evaluation of microbiological properties, a "green" raw material (fibres) which has a high germ load due to its production process was used. The fibre material was mixed with C2PPG1 in different concentrations (0.5 and 2.5 wt %) and the development of germs at room temperature and at 40° C. was tested over a period of 12 weeks according to DIN EN ISO 11930:

The germ development was rated on a scale of 1-5 as follows:

| 1 | satisfactory (no germ development was observed) |
|---|---|
| 3 | acceptable (slight germ development was observed) |
| 5 | not satisfactory (high germ development was observed) |

Figure 2A:
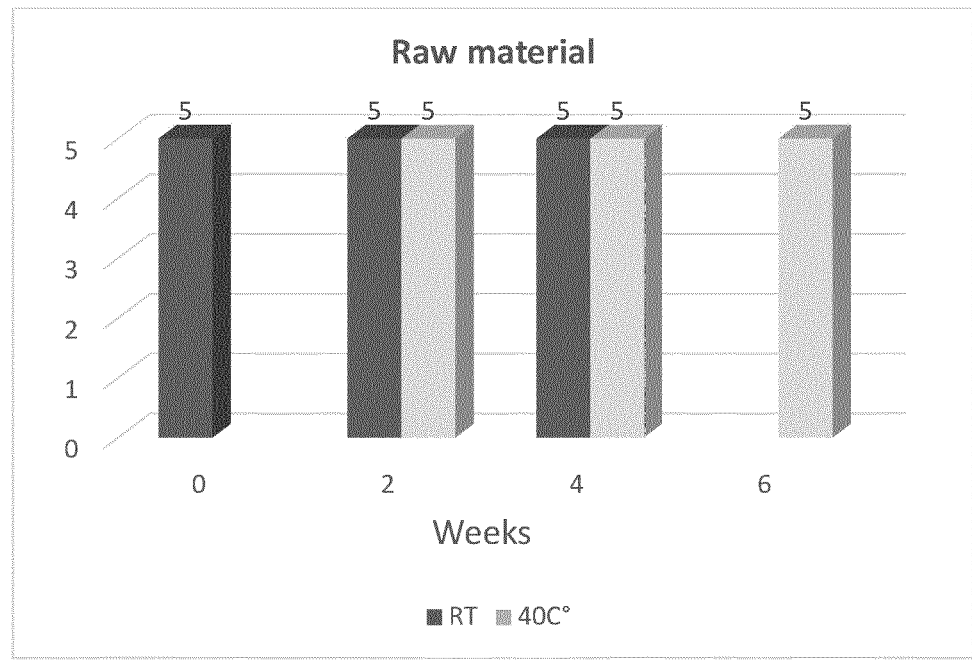
FIG. 2a shows the development of the germ load in a green raw material at room temperature (RT) and 40° C.
Figure 2B:
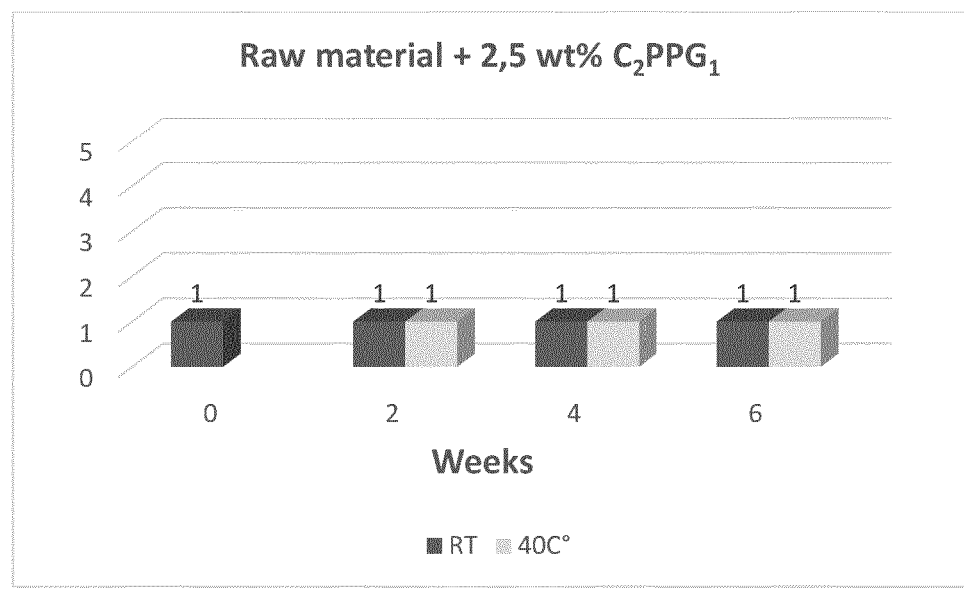
FIG. 2b shows the development of the germ load in a green raw material to which 2.5 wt % C2PPG1 has been added at room temperature (RT) and 40° C.

The results are shown in FIGS. 2a and 2b.

Figure 3:
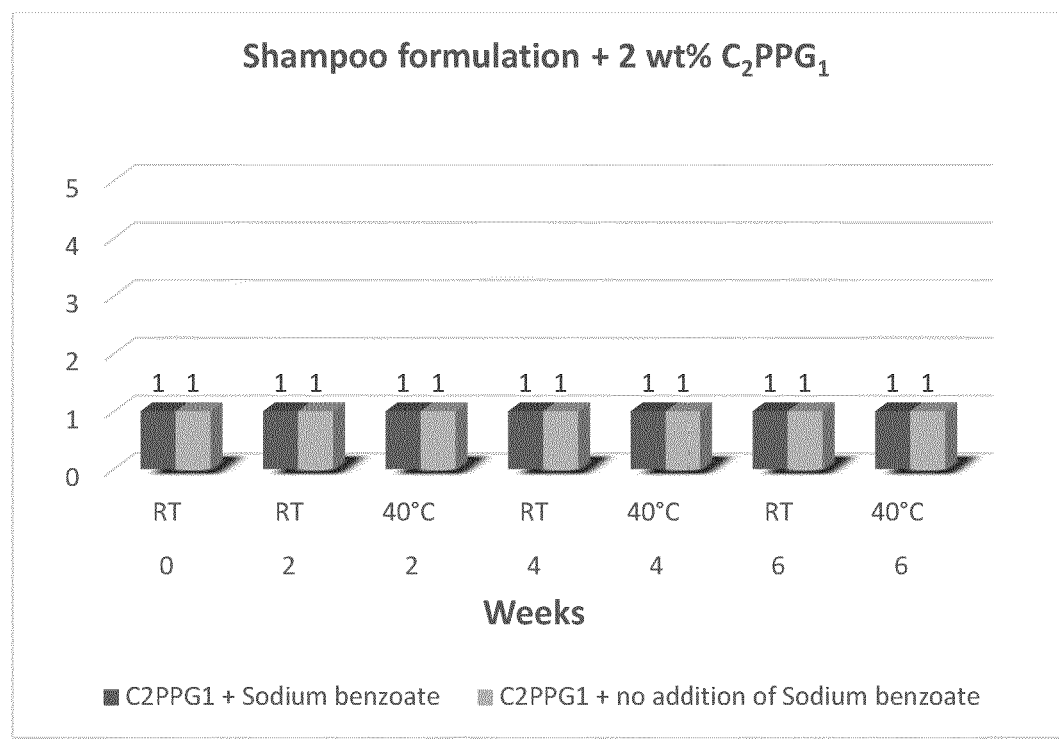
FIG. 3 shows the development of the germ load in a shampoo composition to which 2.0 wt % C2PPG1 has been added at room temperature (RT) and 40° C.

In addition, C2PPG1 was added to a shampoo formulation in a concentration of 2 wt % and the development of germs at room temperature and at 40° C. was tested over a time period of 6 weeks via biomonitoring. The results for shampoo formulation with and without the addition of sodium benzoate were rated in accordance with the scale 1-5 above and are shown in Figure As can be taken from FIGS. 2a and 2b, the addition of 2.5 wt % C2PPG1 significantly reduced the load of germs present in the fibre material. In addition, FIG. 3 shows that the germ load could be stably maintained at a low level. In view of these test results which show a germ load reducing effect, the compounds of the present invention are suitable for use in cosmetic products.

Conclusions:

From the results of the above-mentioned examples, it can be concluded that many compounds of the present invention have several very useful properties and are thus very versatile. They can be used as emulsifiers and/or solubilizers for various oil phases, have anti-corrosive properties or reduce microbial contamination (germ load) of cosmetic products.

The invention claimed is:

1. A compound according to Formula (1)

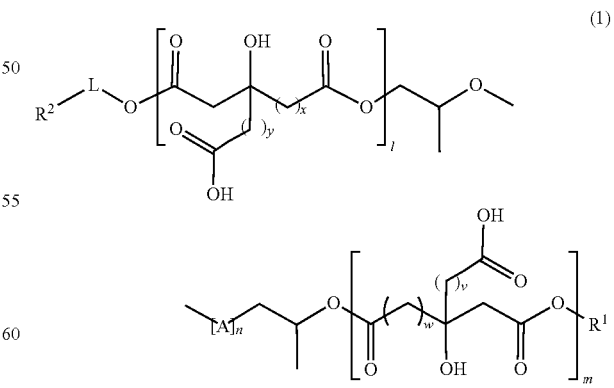

wherein each A is independently represented by [$CH_2CHCH_3O$] or [$CHCH_3CH_2O$];

$R^1$ and $R^2$ each independently are hydrogen, a linear or branched $C_{6-34}$ alkyl group which is optionally substituted with OH, a linear or branched $C_{6-34}$ alkenyl group which is optionally substituted with OH, or a group of the formula $N(R^3)$—$C(=O)$—$R^4$;

L is a direct bond, $C(=O)$, $C_{1-10}$ alkylene or a polypropylene oxide unit of the formula $[A]_{n+2}$;

$R^3$ is H, $C_{1-6}$ alkylene or O—$C_{1-6}$ alkylene;

$R^4$ is a linear or branched $C_{6-34}$ alkyl group which is optionally substituted with OH, or a linear or branched $C_{6-34}$ alkenyl group which is optionally substituted with OH;

n is an integer from 0-50;

m is 0 or 1, l is 0 or 1, with the proviso that at least one of m and l is 1;

x is 0 or 1, y is 0 or 1 and the sum of x and y is 1 and v is 0 or 1, w is 0 or 1 and the sum of v and w is 1.

2. The compound of claim 1, wherein $R^1$ and $R^2$ each independently are hydrogen, a linear or branched $C_{8-20}$ alkyl group which is optionally substituted with OH, a linear or branched $C_{8-20}$ alkenyl group which is optionally substituted with OH, or a group of the formula $N(R^3)$—$C(=O)$—$R^4$; L is a direct bond, $C(=O)$, $C_{2-6}$ alkylene or a polypropylene glycol unit of the formula $[CH_2CH(CH_3)O]_{n+2}$; $R^3$ is hydrogen and $R^4$ is $C_{8-18}$ alkyl or alkenyl.

3. The compound of claim 1, wherein n is an integer from 1-20.

4. The compound of claim 1, wherein y is 0 and x is 1 and/or v is 0 and w is 1.

5. The compound of claim 1, wherein $R^1$ is hydrogen.

6. The compound of claim 1, wherein $R^1$ is hydrogen, $R^2$ is hydrogen, L is a direct bond, m is 0 and l is 1.

7. The compound of claim 1, wherein $R^1$ is hydrogen, $R^2$ is hydrogen, L is a direct bond, m is 1 and l is 1.

8. The compound of claim 1, wherein $R^1$ is hydrogen, $R^2$ is hydrogen, L is $[CH_2CH(CH_3)O]_{n+2}$, m is 0 and l is 1.

9. The compound of claim 1, wherein $R^1$ is hydrogen, $R^2$ is a linear or branched $C_{8-18}$ alkyl group which is optionally substituted with OH, a linear or branched $C_{8-18}$ alkenyl group which is optionally substituted with OH, L is a direct bond, m is 0 and l is 1.

10. The compound of claim 9, wherein $R^2$ is a linear $C_{10-18}$ alkyl group or a $C_{10-18}$ alkylene group.

11. The compound of claim 1, wherein $R^1$ is hydrogen, $R^2$ is a linear or branched $C_{8-20}$ alkyl group which is optionally substituted with OH, a linear or branched $C_{8-20}$ alkenyl group, L is $C(=O)$, m is 1 and l is 0.

12. The compound of claim 11, wherein $R^2$ is a linear $C_{11-17}$ alkyl group.

13. The compound of claim 1, wherein $R^1$ is hydrogen, L is $C_2$ alkylene, $R^2$ is $N(R^3)$—$C(=O)$—$R^4$, $R^3$ is hydrogen, $R^4$ is a linear or branched $C_{8-18}$ alkyl group, or a linear or branched $C_{8-18}$ alkenyl group, l is 1 and m is 0.

14. A composition, comprising at least one compound as defined in claim 1.

15. The composition of claim 14, which further comprises a base oil.

16. A cooling lubricant comprising the compound of claim 1.

17. A cosmetic product comprising the compound of claim 1.

18. A release agent comprising the compound of claim 1.

19. The compound of claim 1, wherein n is an integer from 1-10.

* * * * *